United States Patent [19]

McBrayer et al.

[11] Patent Number: 5,741,285

[45] Date of Patent: Apr. 21, 1998

[54] ENDOSCOPIC INSTRUMENT HAVING NON-BONDED, NON-WELDED ROTATING ACTUATOR HANDLE AND METHOD FOR ASSEMBLING THE SAME

[75] Inventors: Michael Sean McBrayer, Miami; Charles R. Slater, Fort Lauderdale; Juergen Andrew Kortenbach, Miami Springs; Saul Gottlieb, Miami, all of Fla.

[73] Assignee: Symbiosis Corporation, Miami, Fla.

[21] Appl. No.: 667,375

[22] Filed: Jun. 21, 1996

Related U.S. Application Data

[63] Continuation of Ser. No. 284,794, Aug. 2, 1994, abandoned, which is a continuation-in-part of Ser. No. 91,177, Jul. 13, 1993, Pat. No. 5,395,369.

[51] Int. Cl.⁶ ............................................. A61B 17/00
[52] U.S. Cl. ........................... 606/170; 606/46; 606/205
[58] Field of Search ............................... 606/205, 206, 606/170, 174, 51, 52, 46; 128/751

[56] References Cited

U.S. PATENT DOCUMENTS

| | | | |
|---|---|---|---|
| 4,368,734 | 1/1983 | Banko | 606/170 |
| 5,174,300 | 12/1992 | Bales et al. | 128/751 |
| 5,258,006 | 11/1993 | Rydell et al. | 606/205 |
| 5,282,800 | 2/1994 | Foshee et al. | 606/52 |
| 5,286,255 | 2/1994 | Weber | 606/205 X |
| 5,308,358 | 5/1994 | Bond et al. | 606/205 |
| 5,314,424 | 5/1994 | Nicholas | 606/41 |
| 5,330,502 | 7/1994 | Hassler et al. | 606/205 |
| 5,342,381 | 8/1994 | Tidemand | 606/174 |
| 5,344,428 | 9/1994 | Griffiths | 606/205 |
| 5,383,888 | 1/1995 | Zvenyatsky et al. | 606/170 X |

*Primary Examiner*—Michael H. Thaler
*Attorney, Agent, or Firm*—David P. Gordon; Thomas A. Gallagher

[57] ABSTRACT

An actuator for an endoscopic instrument includes a handle having a through bore with a distal keyway and a lever which is pivotally coupled to the handle. A proximal tube sleeve is insert molded or press fit to the proximal end of the instrument tube. The tube sleeve has a pair of ramped thread-like projections and a pair of distally facing wedge-like projections all of which pass through the keyway in the handle. A proximal stop ring on the tube sleeve prevents the tube sleeve from passing completely through the handle. A ferrule having a pair of interior threadlike projections threadably engages the tube sleeve and is frictionally engaged by the wedge-like projections. A ferrule locking cap having a proximal inner groove and a distal flange fits in the annular space between the tube sleeve and the ferrule. The proximal groove engages a locking ring on the tube sleeve and splines on the tube sleeve and the ferrule frictionally engage the cap. The tube sleeve and the ferrule engage the cap with some friction so that the tube may be rotated relative to the handle but will not rotate relative to the ferrule.

20 Claims, 14 Drawing Sheets

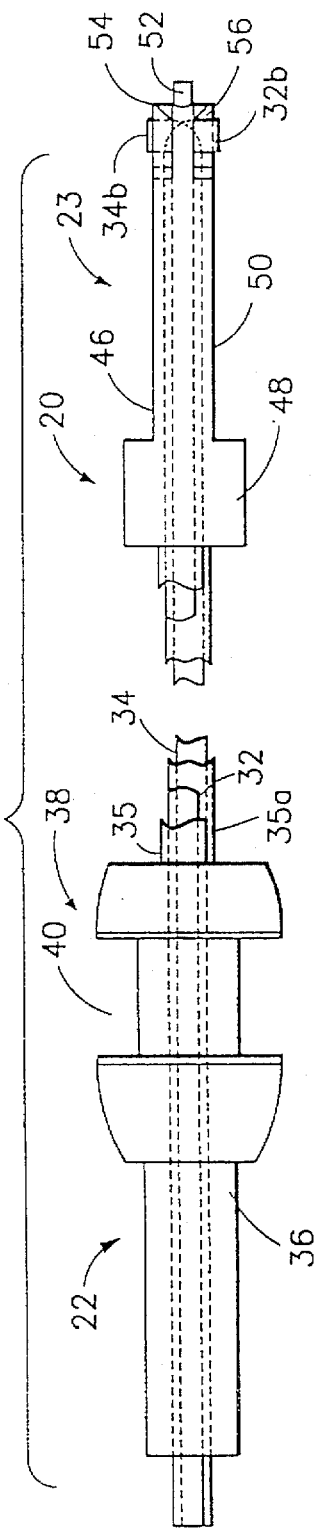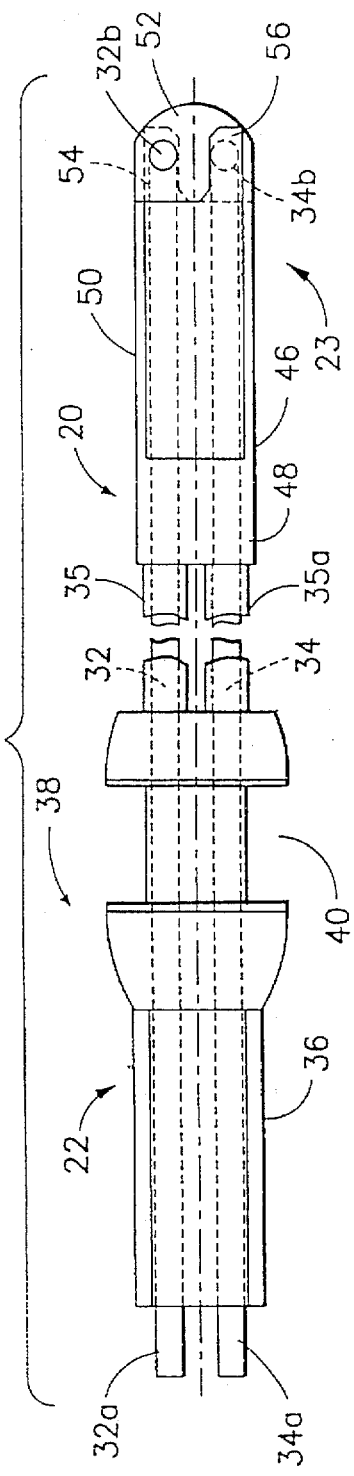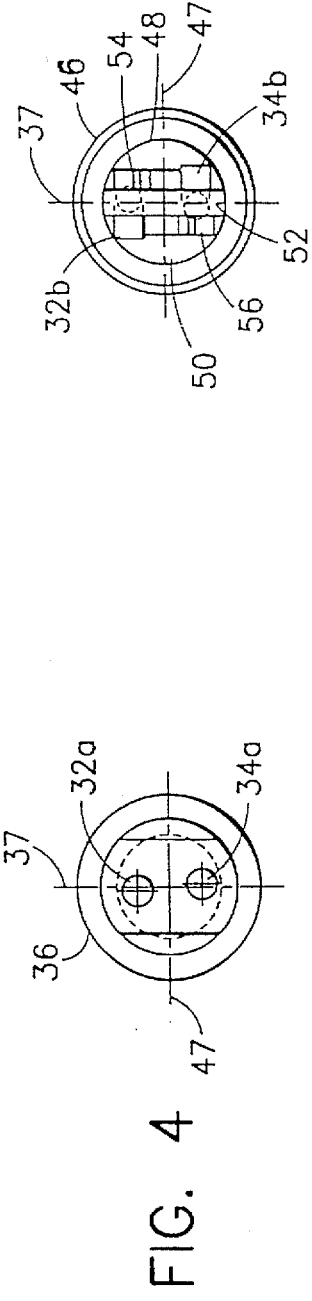

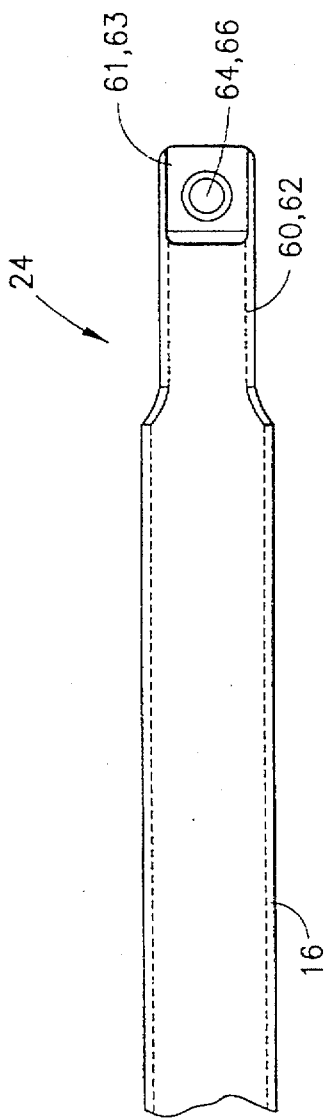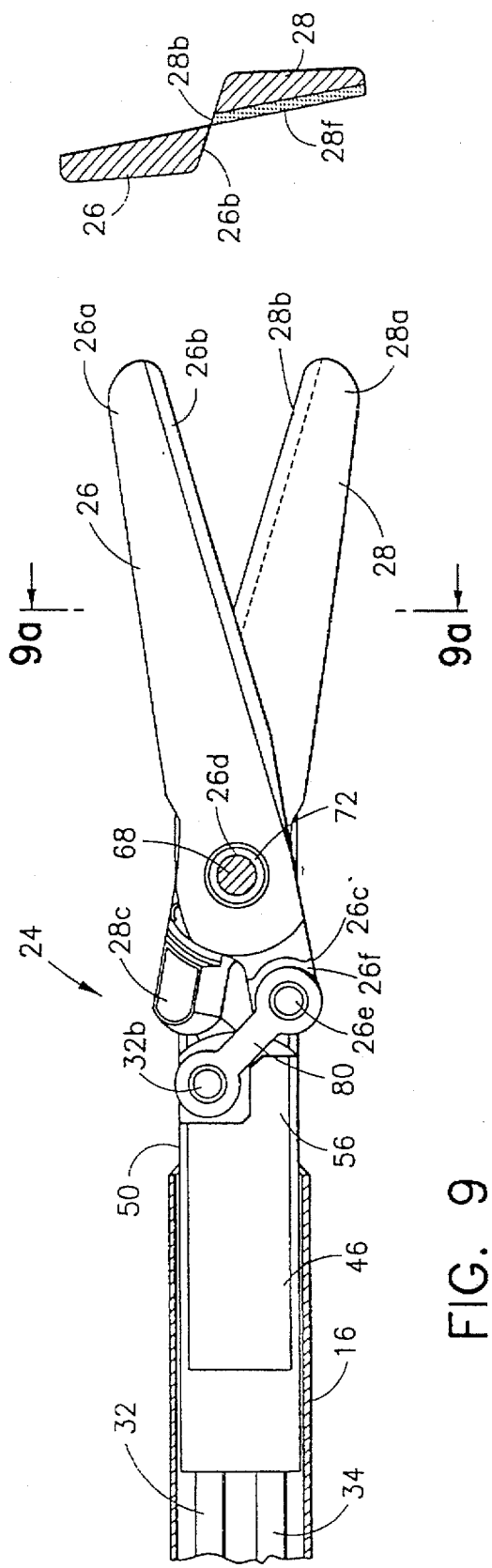

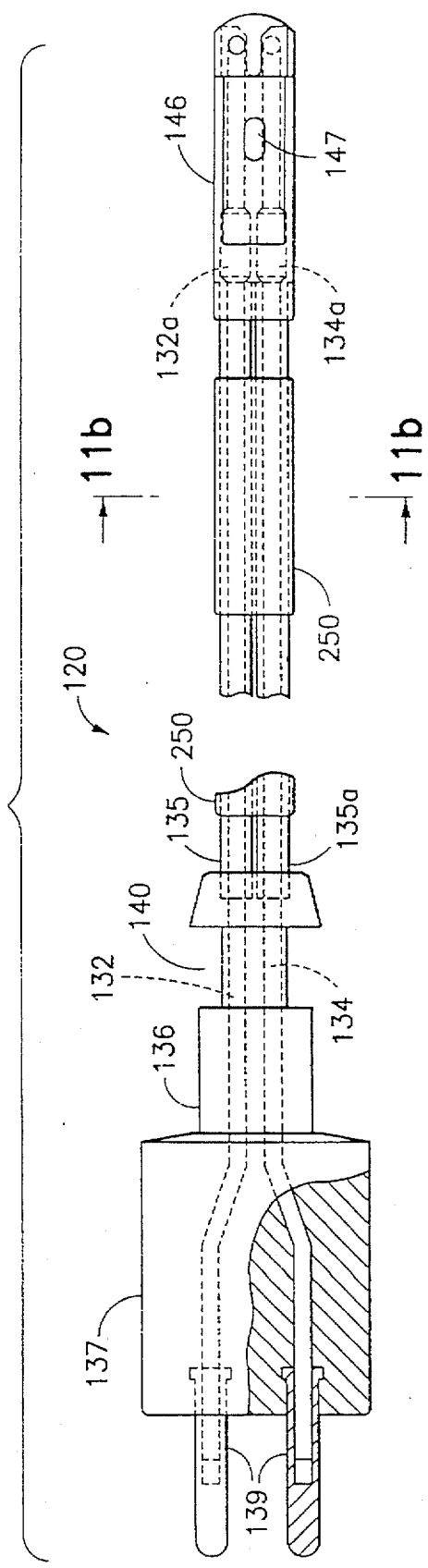
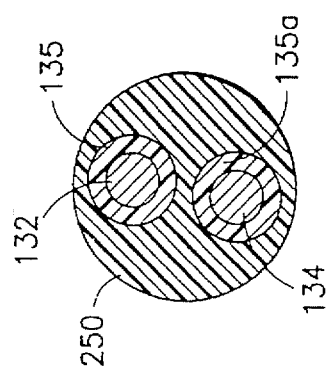
FIG. 11a
FIG. 11b

ENDOSCOPIC INSTRUMENT HAVING NON-BONDED, NON-WELDED ROTATING ACTUATOR HANDLE AND METHOD FOR ASSEMBLING THE SAME

This application is a continuation of Ser. No. 08/284,794 filed Aug. 2, 1994, now abandoned, which is a continuation-in-part of application Ser. No. 08/091,177 filed Jul. 13, 1993 now U.S. Pat. No. 5,395,369.

This application is related to co-assigned U.S. Pat. No. 5,174,300 (Endoscopic Surgical Instruments Having Rotatable End Effectors), the complete disclosure of which is incorporated herein by reference.

BACKGROUND OF THE INVENTION

1. Field of the Invention

This invention relates to endoscopic surgical instruments More particularly, the present invention relates to double acting endoscopic scissors having bipolar cautery capability and to an endoscopic instrument handle with a non-bonded, non-welded ferrule which facilitates a rotating of the tube, clevis, and end effectors relative to the handle.

2. State of the Art

Endoscopic surgery is widely practiced throughout the world today and its acceptance is growing rapidly. In general, endoscopic surgery involves one or more incisions made by trocars where trocar tubes are left in place so that endoscopic surgical instruments may be inserted through the tubes. A camera or magnifying lens is often inserted through one trocar tube, while a cutter, dissector, or other surgical instrument is inserted through another trocar tube for purposes of manipulating and/or cutting the internal organ. Sometimes it is desirable to have several trocar tubes in place at once in order to receive several surgical instruments. In this manner, organs or tissue may be grasped with one surgical instrument, and simultaneously may be cut with another surgical instrument; all under view of the surgeon via the camera.

By 1996, it is expected that more than two million additional endosurgeries will be performed per year that, in 1990, were done via open surgery (MedPRO Month, I:12, p. 178). The advantages of endoscopic surgery are clear in that it is less invasive, less traumatic and recovery is typically quicker. As a result, many new instruments and devices for use in endosurgery are introduced every year.

Endoscopic surgical instruments generally include a tube, a push rod which extends through the tube, an actuating means engaging the tube and the push rod for imparting reciprocal axial motion to the push rod, end effector means (typically two end effectors) coupled to the push rod by linkage means, and a clevis coupled to the tube at its proximal end and to the end effector means at its distal end, wherein axial movement of the push rod effects movement of the end effector means in a plane parallel to the longitudinal axis of the push rod. For purposes herein, the "distal end" of a surgical instrument or any part thereof, is the end most distant from the surgeon and closest to the surgical site, while the "proximal end" of the instrument or any part thereof, is the end most proximate the surgeon and farthest from the surgical site. The end effectors may be grippers, cutters, forceps, scissors, etc.

Endoscopic instruments may be generally classified as either "single acting" or "double acting". In a single acting instrument, a stationary end effector is coupled to the distal end of the tube and a movable end effector is coupled to the distal end of the push rod and is mounted for rotation relative to the stationary end effector. In single acting instruments, a clevis is not required. It is only necessary to provide a rotational coupling between the stationary end effector and the movable end effector. In double acting instruments, two end effectors are mounted for rotation in a clevis which is coupled to the distal end of the tube; and both end effectors are coupled to the distal end of the push rod.

Many endoscopic instruments are provided with cautery capability. Endoscopic cautery instruments may be monopolar or bipolar. In monopolar instruments, both end effectors are electrically coupled to a single pole of a source of cautery current. RF energy is conducted from the end effectors through the patient's body to a remote "body plate". In bipolar instruments, each end effector is coupled to a separate pole of a source of cautery current. RF energy is conducted from one end effector through the patient's body to the other end effector. Monopolar instruments suffer from the fact that the return path between the end effectors and the large area body plated can be unpredictable as the electrical current seeks the path of least resistance. With bipolar instruments, however, the path of the current is very short, from one end effector to the other, and involves only the tissue and fluids in the short path between the electrodes. However, bipolar endoscopic instruments are difficult to manufacture. The end effectors must be electrically insulated from each other and some means must be found to provide a separate electrical connection to each end effector. These problems are most acute in the construction of endoscopic scissors which have blades in virtually constant contact with each other.

European Patent Number 0 572 131 A1 to Rydell discloses surgical scissors with a bipolar coagulation feature. Rydell's scissors are single acting. A first scissor blade is mounted on the distal end of a hollow tube and a second blade is pivotally mounted to the first scissor blade. A rigid conductive wire or rod is coupled to the second scissor blade and extends through the hollow tube. The blades are constructed of metal blanks with bonded ceramic insulators insulating the blades from each other along their entire lengths. An insulating pivot member pivotally couples the second blade to the first blade. The rigid rod is covered with an insulating material. Scissor handles are coupled to the proximal ends of the tube and the rod. A first lead wire is coupled to the proximal end of the rod and a second lead wire is coupled to the interior of the hollow tube by means of a copper wave spring entering the proximal end of the tube. As mentioned above, the scissors are single acting, one blade moves as the other remains stationary. The movable blade is pivotally coupled to the stationary blade by a non-conductive screw which enters a threaded opening in the stationary blade or by a conductive screw which enters an insulated threaded opening in the stationary blade.

Rydell's scissors are difficult to manufacture. The blades must be made of ceramic bonded metal blanks. The electrical and mechanical couplings are complex and intricate. Providing threads in the stationary blade requires that it be relatively thick and weakens the construction considerably. Rydell's scissors do not present a workable solution to the problems of bipolar scissors. Additionally, Rydell's design is limited in other ways in that the scissors are not double acting and the blades cannot be rotated relative to the longitudinal axis of the tube.

European Patent Number 0 518 230 A1 to Eggers discloses bipolar electrosurgical endoscopic instruments including double acting bipolar endoscopic scissors. Eggers' scissors have an actuating handle coupled to the proximal ends of a tube and push rod and a pair of double acting scissor blades coupled to the end of the tube. The distal end of the push rod is coupled to the scissor blades for rotating them relative to each other. The tube and the push rod are rotationally mounted in the handle so that the tube and the push rod are rotatable about the longitudinal axis of the tube. Eggers achieves a bipolar coupling through the push rod alone. Eggers' push rod is a composite of two semicylindrical halves bonded to each other with an insulating layer between them. The insulating layer also covers the outer surface of the push rod to insulate it from the inner surface of the tube. The distal end of the push rod is slotted so as to provide a bipolar fork, each tine being the distal end of one semicylindrical half of the push rod. Facing surfaces of the tines are not insulated and provide the electrical contact surfaces for electrical coupling with the scissor blades. The distal end of the tube has a similar slot for mounting the scissor blades. The scissor blades each have a pivot hole and a slotted shank portion and at least one of the blades is coated with electrical insulation on the surface which faces the other blade. The outer surfaces of the shank portions are not insulated. The scissor blades are mounted on a non-conductive pivot pin which engages a hole transverse to the slot in the distal end of the tube. The slotted shank portions of the blades enter the space between the tines of the push rod and are coupled to the push rod by a nonconductive pivot pin which enters the slots of the shanks and engages a hole in each tine. Movement of the push rod relative to the tube moves the pivot pin in the slots of the shanks of the blades and causes them to rotate about the pivot pin in the tube. The outer surfaces of the slotted shanks rub against the inner surfaces of the tines and make electrical contact therewith. The inner surface of at least one shank is coated to insulate it from the other shank.

Eggers' bipolar scissors present interesting ideas, but they also are difficult to manufacture and are unlikely to be functional. The construction of the bipolar push rod is complicated. The electrical connection between the push rod and the scissor blades is dependent on a good frictional engagement between the tines of the push rod and the shanks of the scissor blades and can weaken over time. In addition, the number of pivot pins and insulators is excessive, thereby making the assembly of the distal end of the device intricate.

It is well known to provide an endoscopic instrument handle with a ferrule for rotating the tube and clevis (and thus the end effectors) relative to the handle. Some of these ferrules usually include biasing springs and locking mechanisms so that the tube does not freely rotate out of a selected position. These locking ferrule arrangements require the practitioner to slide the ferrule against a biasing spring while rotating the tube of the instrument. In addition, many commonly used ferrules are either welded or otherwise bonded to the hollow tube of the endoscopic instrument. In order to allow rotation of the hollow tube relative to the handle, a certain amount of axial play is permitted between the handle and the tube. This axial play results in what is known as "slop", i.e. undesired movement of the tube in response to movement of the actuator lever in the handle. Slop decreases the responsiveness of the end effectors. Also, in the case of cautery instruments, it is important that the ferrule coupling be non-conductive.

SUMMARY OF THE INVENTION

It is therefore an object of the invention to provide a double acting bipolar endoscopic scissors.

It is also an object of the invention to provide a bipolar endoscopic scissors wherein the scissor blades are rotatable about the longitudinal axis of the instrument tube.

It is another object of the invention to provide a bipolar endoscopic scissors which has relatively thin blades.

It is still another object of the invention to provide a bipolar endoscopic scissors which uses a bipolar push rod which is easy to manufacture.

It is yet another object of the invention to provide a bipolar endoscopic scissors with a reliable electrical connection between the bipolar push rod and the scissor blades.

It is also an object of the invention to provide a bipolar endoscopic scissors which has enhanced cutting strength.

It is another object of the invention to provide an endoscopic instrument handle having a ferrule for rotating the end effectors relative to the handle where the ferrule is not bonded or welded to the outer tube of the instrument.

It is still another object of the invention to provide a ferrule arrangement for rotating the end effectors of an endoscopic instrument which is simple in design and inexpensive to manufacture.

It is also an object of the invention to provide a ferrule arrangement which is composed of all non-conductive materials.

It is another object of the invention to provide a ferrule arrangement which reduces slop in the outer tube of an endoscopic instrument.

In accord with these objects which will be discussed in detail below, the double acting bipolar endoscopic scissors of the present invention includes a hollow tube having a proximal end and a distal end, a bipolar push rod extending through the hollow tube, a pair of scissor blades coupled to the bipolar push rod, and a handle and actuator lever coupled to and rotatable relative to the push rod and the tube. The bipolar push rod includes a pair of spaced apart stainless steel rods which are covered with a shrink wrapped insulation along substantially all of their length except for a portion of their proximal and distal ends. The rods are insert molded in a distal polypropylene collar near their distal ends, in a proximal polypropylene collar near their proximal ends, and in a plurality of polypropylene disks or cylinders at intervals around the insulated rods between the proximal and distal collars. The disks prevent buckling of the rods or helical twisting of the rods over one another.

According to preferred aspects of the invention, the distal collar is cylindrical at its proximal end with a flattened vane extending distally therefrom. The distal ends of the rods are bent approximately 90 degrees and exit the flattened vane near the distal end of the distal collar which is provided with surrounding steps. The proximal collar is substantially cylindrical with a radial groove and the proximal ends of the rods extend from the proximal end of the proximal collar. The radial groove in the proximal collar engages an annular disk mounted in a spherical opening in the manual actuation lever and the outer diameter of the cylindrical portion of the distal collar closely matches the interior diameter of the hollow tube. Movement of the manual actuation lever results in translational movement of the push rod relative to the hollow tube and the annular groove engagement of the proximal collar with the manual actuation lever allows for rotation of the push rod relative to the manual actuation lever. The distal end of the hollow tube is provided with an integral clevis having diametrical mounting holes. A pair of scissor blades, each having a distal cutting surface, a proximal tang, and a central mounting hole are mounted in the clevis with an axle screw and a nut. The proximal tangs of the scissor blades are coupled by links to the bent distal ends of the rods which extend from the flattened portion of the distal collar. In order to electrically insulate each scissor blade from the other and from the hollow tube, a flanged bushing is provided between the axle screw and the blades, and a plastic insulator is provided between the blades and the tube.

Additional preferred aspects of the invention include: coating the scissor blades with plasma sprayed aluminum oxide, and offsetting the rods in the distal collar relative to a diametrical axis of the collar. The offset provides more room to couple the rods to the scissor blades and also gives mechanical advantage to the scissors.

According to another aspect of the invention, a nonconductive ferrule coupling for rotating the handle relative to the end effectors is provided where the ferrule coupling is neither bonded nor welded to the outer tube of the endoscopic instrument. A preferred ferrule coupling includes a cylindrical glass filled polycarbonate tube collar, a glass filled polycarbonate ferrule, and a polypropylene or polyurethane ferrule locking cylinder or cap having a circular interior groove. The cylindrical tube collar is preferably insert molded on the proximal end of the hollow tube, and is provided with a proximal stop, a central thread-like key, and a distal locking ring. The distal end of the handle has a corresponding keyway through which the thread-like key of the tube collar passes but through which the stop cannot pass. The ferrule is provided with an interior thread which is broken by a keyway. During assembly, the ferrule slips over the thread-like key of the tube collar and is twisted into a locking engagement with the tube collar until axial slop is eliminated. The ferrule locking cylinder is then slid and force fit into the distal end of the ferrule so that it engages both the tube collar locking ring with its interior groove and the ferrule.

According to preferred aspects of the handle arrangement, a preferred coupling between the actuating lever and the proximal collar of the push rod includes a pair of nylon or glass filled polycarbonate L-shaped members, each having a notched cylindrical base. The actuating lever has a U-shaped cut-out in its top portion which is transected by a circular bore. The proximal collar of the push rod is placed in the U-shaped cut-out of the actuating lever so that its radial groove is aligned with the circular bore. The two L-shaped members are inserted through opposite sides of the circular bore so that they engage upper and lower portions of the radial groove in the proximal collar of the push rod and they engage the notch in each other's cylindrical base. The cylindrical bases engage the circular bore in the actuating lever.

Additional objects and advantages of the invention will become apparent to those skilled in the art upon reference to the detailed description taken in conjunction with the provided figures.

BRIEF DESCRIPTION OF THE DRAWINGS

FIG. 2 is an enlarged broken top view of a first embodiment of the push rod assembly of the bipolar scissors of FIG. 1;

FIG. 3 is an enlarged broken side elevation view of the push rod assembly of FIG. 2;

FIG. 4 is an enlarged proximal end view of the push rod assembly of FIG. 3;

FIG. 5 is an enlarged distal end view of the push rod assembly of FIG. 3;

FIG. 8 is an enlarged broken side elevation view of the distal end of the tube of the bipolar scissors of FIG. 1;

FIG. 9 is an enlarged broken side elevation view in partial section of the distal end of the bipolar scissors of FIG. 1 with the scissor blades in the open position;

FIG. 9a is a cross section along line 9a—9a in FIG. 9.

FIG. 11a is a view similar to FIG. 3, of a second embodiment of the push rod assembly;

FIG. 11b is a cross section along line 11b—11b in FIG. 13a;

DETAILED DESCRIPTION OF THE PREFERRED EMBODIMENTS

Figure 1:
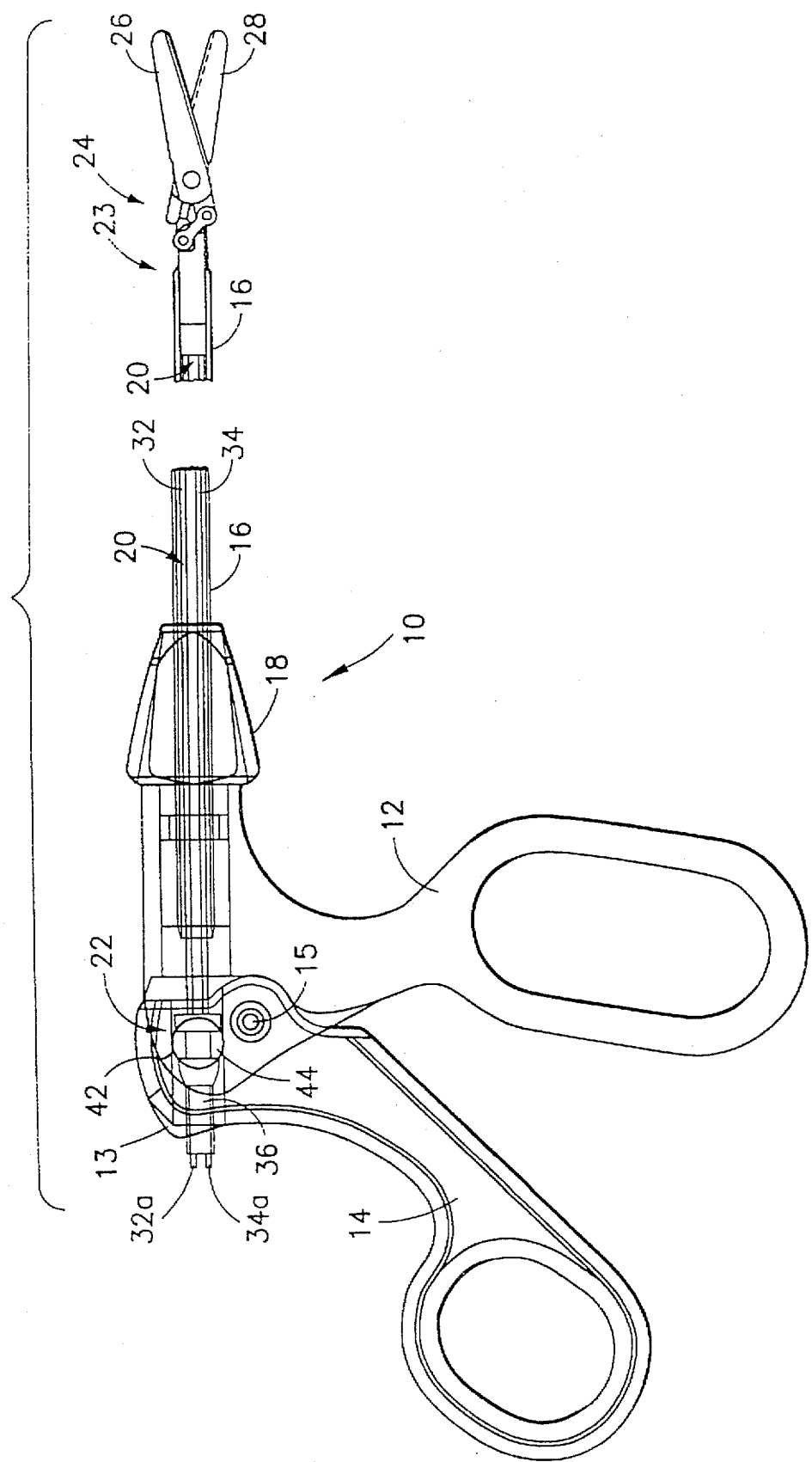
FIG. 1 is a broken transparent side elevation view of a first embodiment of the endoscopic bipolar scissors of the invention.
Figure 10:
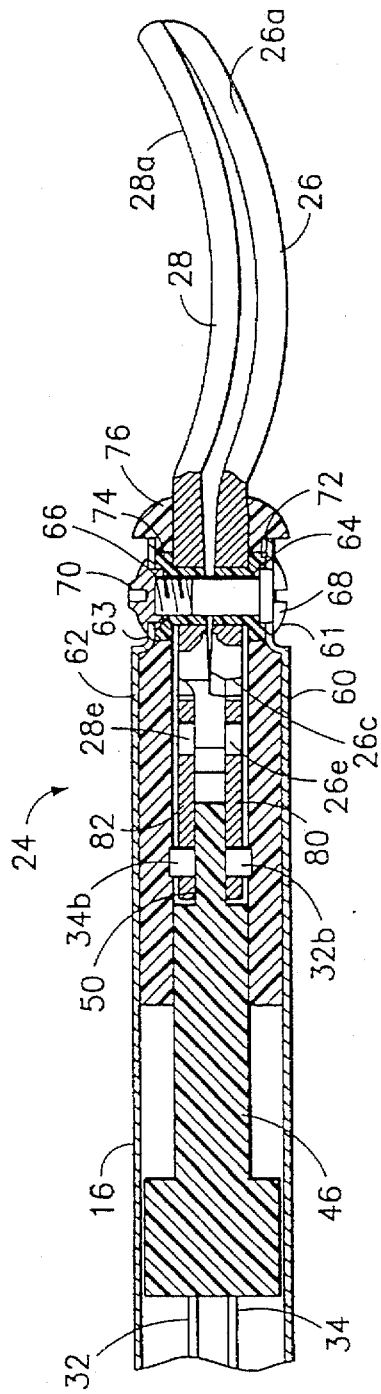
FIG. 10 is an enlarged broken top view in partial section of the distal end of the invention with the scissor blades in the closed position.

Turning now to FIG. 1, a first embodiment of the double acting bipolar endoscopic scissors 10 according to the invention includes a proximal handle 12 with a manual lever actuator 14 pivotally coupled to the handle by a pivot pin 15. A hollow stainless steel tube 16 is rotatably coupled to the handle 12 and is preferably rotatable about its longitudinal axis relative to the handle 12 through the use of a ferrule 18 such as described in detail in co-assigned U.S. Pat. No. 5,174,300. A push rod assembly 20 extends through the hollow tube 16 and is coupled at its proximal end 22 to the manual lever actuator 14 as described in more detail below. The distal end of the tube 16 has an integral clevis 24 within which a pair of super alloy scissor blades 26, 28 are mounted on an axle screw 68 (FIGS. 9 and 10). As will be described in more detail below, the distal end 23 of the push rod assembly 20 is coupled to the scissor blades 26, 28 so that reciprocal movement of the push rod assembly 20 relative to the tube 16 opens and closes the scissor blades 26, 28. It will be appreciated that the reciprocal movement of the push rod assembly 20 relative to the tube 16 is effected by movement of the manual lever actuator 14 relative to the handle 12.

Referring now to FIGS. 2 through 5, the push rod assembly 20 is seen to include a first stainless steel rod 32, a second stainless steel rod 34, a proximal polypropylene collar 36, and a distal polypropylene collar 46. The proximal end 22 of the push rod assembly 20 includes the proximal polypropylene collar 36 into which the rods 32, 34 of approximately 0.040 inch diameter are insert molded so that their proximal ends 32a, 34a extend beyond the proximal end of the proximal collar 36. The proximal collar 36 is provided with a substantially cylindrical or spherical portion 38 having a radial groove 40. The manual lever actuator 14 (FIG. 1) is provided with a substantially spherical opening 42 and the proximal collar 36 is coupled to the lever actuator 14 by an annular disk 44 which engages the radial groove 40 and the spherical opening 42. Those skilled in the art will appreciate, therefore, that the proximal end 22 of the push rod assembly 20 is thus rotatably mounted relative to the manual actuation lever 14. The relative dimensions of the collar 36, the lever 14, and the first and second rods 32, 34 are such that the proximal ends 32a, 34a of the rods extend through the lever 14 and are exposed for coupling with an electrical connector (not shown). The lever actuator 14 is also provided with a slot 13 which is orthogonally arranged relative to the pivot 15 and allows the proximal end of the push rod assembly to extend through the lever without interfering with the movement of the lever.

The distal end 23 of the push rod assembly 20 includes the distal polypropylene collar 46 into which the rods 32, 34 are insert molded. The distal collar 46 has a proximal cylindrical portion 48 and a distally extending flattened vane portion 50 terminating in a narrow distal step 52. The overall length of the distal collar is approximately 0.64 inches with the proximal cylindrical portion being approximately 0.15 inches long and having an outer diameter of approximately 0.168 inches. The flattened vane portion is approximately 0.09 inches thick and the distal step is approximately 0.035 inches thick. As seen best in FIGS. 3 and 5, the distal ends 32b, 34b of the rods 32, 34 are bent approximately 90 degrees in opposite directions and exit the distal collar 46 on the narrow distal step 52. The bent distal ends 32b, 34b each extend approximately 0.325 inches out from the surface of the step 52. It will be appreciated from a careful viewing of FIGS. 3 and 5 that two diametrically opposite portions 54, 56 of the vane 50 extend alongside of the step 52 adjacent the respective distal ends 34b, 32b of the rods 34, 32. According to the presently preferred embodiment of the invention, the rods 32, 34 are each covered by tubes 35, 35a along substantially their entire length between the proximal collar 36 and the distal collar 46. The tubes 35, 35a are preferably formed from a polyolefin (e.g. polyethylene or polypropylene) or a polyphthalamide (e.g. AMODEL manufactured by Amoco).

A careful viewing of FIGS. 3 through 5 will also reveal that the rods 32, 34 are offset relative to both the vertical axes 37 and the horizontal axes 47 of the proximal and distal collars 36, 46. In particular, each rod is offset in a direction opposite to the direction in which its distal end exits the distal collar. The amount of the offset relative to the intersection of the axes is approximately 6.7 degrees and the distance between the central axis of each rod is approximately 0.086 inches. This offset of the rods 32, 34 relative to the axes 37, 47 of the collars 36, 46 provides more room in the distal collar 46 for the ninety degree bend in each rod and the vertical spacing of the rods gives the scissors more mechanical advantage.

Figure 6:
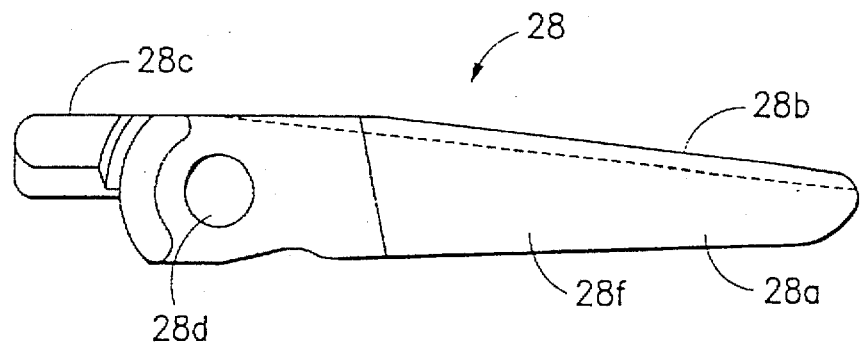
FIG. 6 is side elevation view of a first scissor blade of the bipolar scissors of FIG. 1 according to the invention.
Figure 6A:
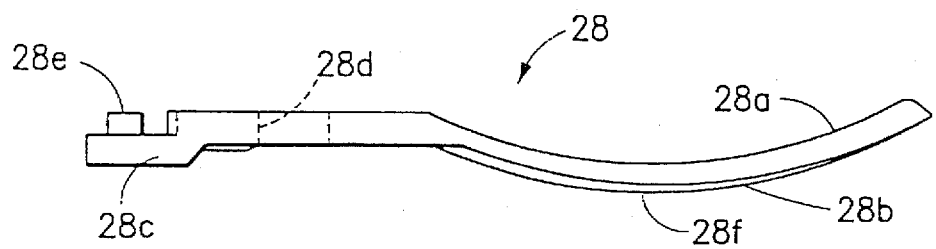
FIG. 6a is a top view of the scissor blade of FIG. 6.

Referring now to FIGS. 6 and 6a, the "inner" scissor blade 28 has a curved distal portion 28a with an upper cutting edge 28b, an upper proximal tang 28c, and a mounting hole 28d therebetween. A connecting lug 28e extends orthogonally from the surface of the tang 28c in the same direction as the curve of the curved distal portion 28a. The overall length of the blade 28 is preferably 0.968 inches. The thickness of the preferred blade is approximately 0.035 inches not including the lug 28e.

Figure 7:
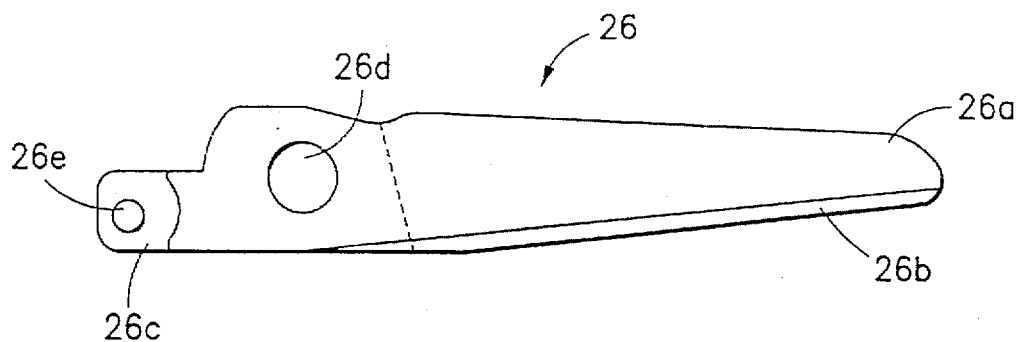
FIG. 7 is side elevation view of a second scissor blade of the bipolar scissors of FIG. 1 according to the invention.
Figure 7A:
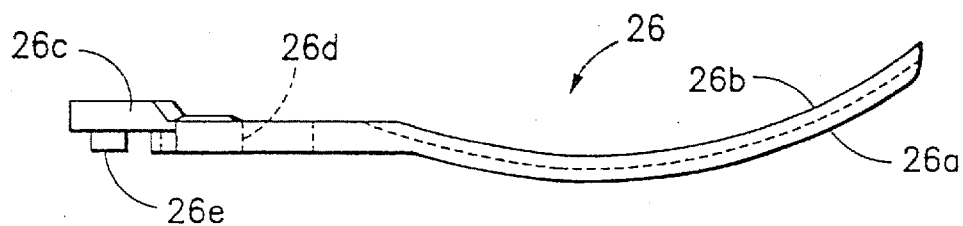
FIG. 7a is a top view of the scissor blade of FIG. 7.

FIGS. 7 and 7a show the mating "outer" scissor blade 26 is configured similarly to the "inner" scissor blade and has a curved distal portion 26a with a lower cutting edge 26b, a lower proximal tang 26c, and a mounting hole 26d therebetween. A connecting lug 26e extends orthogonally from the surface of the tang 26c in the opposite direction to the curve of the curved distal portion 26a. The overall length of the blade 26 is preferably 0.962 inches. The preferred thickness of the blade is also approximately 0.035 inches not including the lug 26e. The inner blade 28 is coated with an electrically insulating ceramic coating 28f over its entire outer face, i.e., the part of the blade which contacts the outer blade 26. This feature is seen best in FIG. 9a where it can be seen that the cutting edge 28b is actually ceramic.

Turning now to FIGS. 8 through 10, the integral clevis 24 at the distal end of the stainless steel tube 16 includes a pair of parallel arms 60, 62 each having a distal end 61, 63 which is narrowed inward as seen best in FIGS. 8 and 10. Axle holes 64, 66 are provided in each of the respective arms 60, 62, at their respective distal ends 61, 63. The scissor blades 26, 28 are mounted between the clevis arms 60, 62 by a stainless steel screw 68 which passes through the mounting holes 26d, 28d of the scissor blades and the axle holes 64, 66 of the clevis arms 60, 62. The screw 68 is secured by a nut 70, and both the screw and the nut are electrically insulated from the scissor blades by a pair of hard coated aluminum flanged insulating bushings 72, 74. The scissor blades are electrically insulated from the clevis arms 60, 62 by a plastic (polyethylene or polypropylene) clevis insulator 76. As seen in FIG. 10, the distal end of the clevis insulator 76 is provided with a broad rounded face having an outer diameter substantially the same as the outer diameter of the tube 16. The screw 68 and the nut 70 reside in the recessed area of the inwardly narrowed ends 61, 63 of the clevis arms 60, 62. The distal ends 32b, 34b of the rods 32, 34 are electrically and mechanically coupled to the connecting lugs 26e, 28e of the scissor blades 26, 28 by conductive links 80, 82. Referring to FIGS. 9, 2, and 5, it will be appreciated that the diametrically opposite portions 54, 56 of the vane 50 prevent rotation of the links 80, 82 around the distal ends 32b, 34b of the rods 32, 34 beyond the point shown in FIG. 9 when the blades 26, 28 are in the open position. The connecting lugs 26e, 28e and the links 80, 82 are preferably coated with silicone grease to protect them from saline solution during a surgical procedure.

With reference to FIGS. 1, 3 and 10, those skilled in the art will appreciate that a bipolar source of cautery current (not shown) applied to the proximal ends 32a, 34a of the rods 32, 34 is conducted through the rods to respective blades 26, 28. The insulating collars 36, 46, the tubing 35, 35a, the bushings 72, 74, and the clevis insulator 76 all serve to prevent a short circuit between the two conductive rods 32, 34 and the blades 26, 28.

FIGS. 11 through 15a show a second embodiment of the double acting bipolar scissors 110 in various stages of assembly. This second embodiment of the invention relates primarily to the handle 112, the actuator lever 114, the tube 116, the ferrule 118, the push rod assembly 120, and the clevis insulator 176. The distal end of the tube 116 and the scissor blades are not shown in these Figures because they are the same as in the first embodiment described above.

Figure 11:
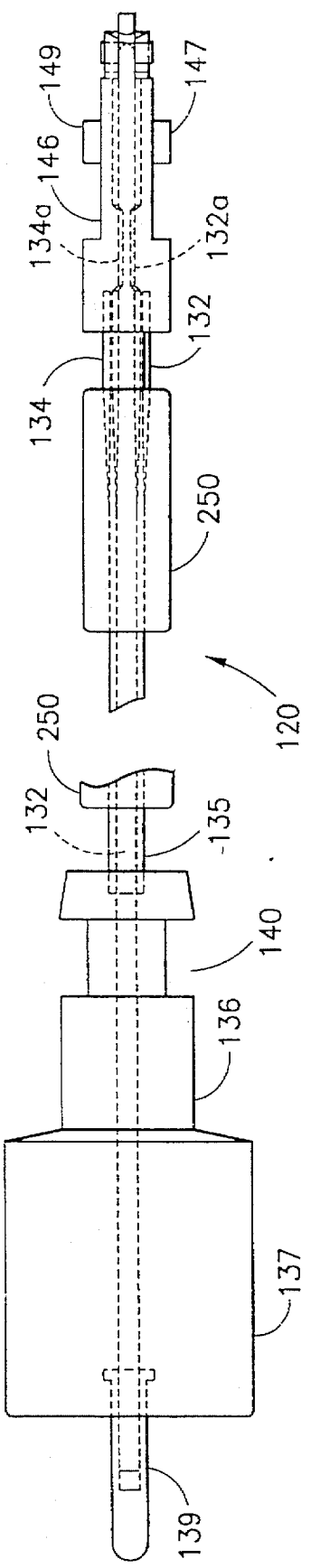
FIG. 11 is a view similar to FIG. 2, of a second embodiment of the push rod assembly.
Figure 11C:
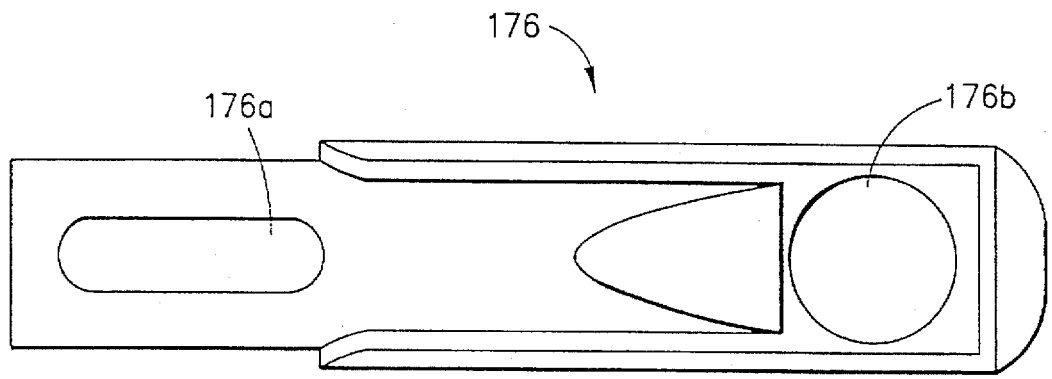
FIG. 11c is a side elevation view of a second embodiment of a clevis insulator.
Figure 11D:
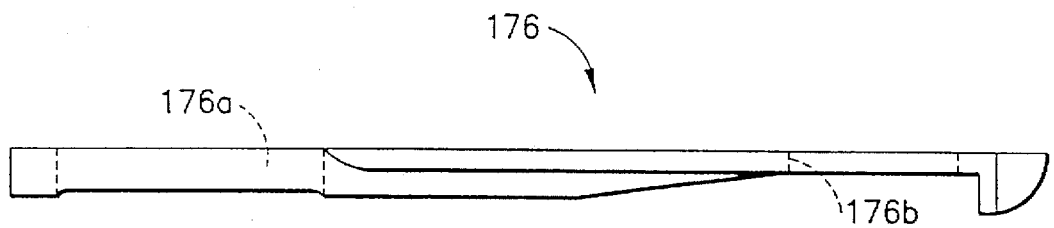
FIG. 11d is a top view of the clevis insulator of FIG. 11c.

Turning specifically to FIGS. 11, 11a, and 11b, a second embodiment of the push rod assembly 120 is shown with a pair of stainless steel rods 132, 134 which are molded into a proximal collar 136 and a distal collar 146. The proximal collar has a radial groove 140 in its distal portion and an increased diameter proximal portion 137 which carries a pair of electrical coupling pins 139 which are electrically coupled to the rods 132, 134. As shown, the pins 139 are spaced farther apart from each other than the rods 132, 134 so as to accommodate a standard cautery connector. The rods 132, 134 are covered with insulating HDPE tubes 135, 135a along substantially their entire length between the proximal and distal collars 136, 146. A plurality of spaced apart polypropylene cylinders 250 are molded about the rods between the proximal collar 136 and the distal collar 146. These cylinders stabilize the rods against helical twisting when the tube 116 (or 16) is rotated as described herein above and below, and by being discontinuous, prevent against warping of the push rod assembly. The distal collar 146 has a pair of guiding wings 147, 149 which engage slots in the clevis insulator described below with reference to FIGS. 11c and 11d. A portion 132a, 134a of each rod 132, 134 which is molded into the distal collar 146 is flattened to stabilize the collar relative to the rods. It will be appreciated that this second embodiment of the push rod assembly can be used with the first embodiment of the handle and ferrule described above with reference to FIG. 1 or with the second embodiment of the handle and ferrule. When this push rod assembly is used, a pair of clevis insulators 176, as shown in FIGS. 11c and 11d, is used. Each clevis insulator 176 has a proximal side slot 176a and a distal bushing hole 176b. A pair of clevis insulators 176 are placed in the clevis as shown in FIG. 10. The side slots 176a are engaged by the guiding wings 147, 149 shown in FIGS. 11 and 11a.

Figure 12:
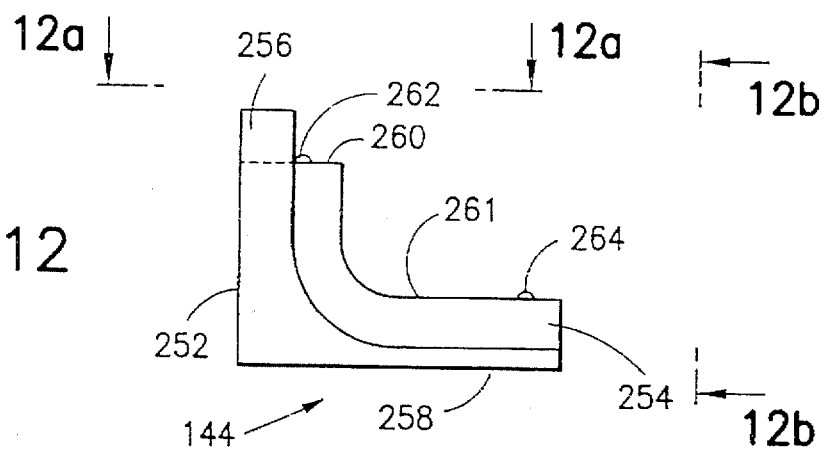
FIG. 12 is an enlarged side elevation view of one of a pair of coupling members for coupling the push rod to the actuator lever.
Figure 12A:
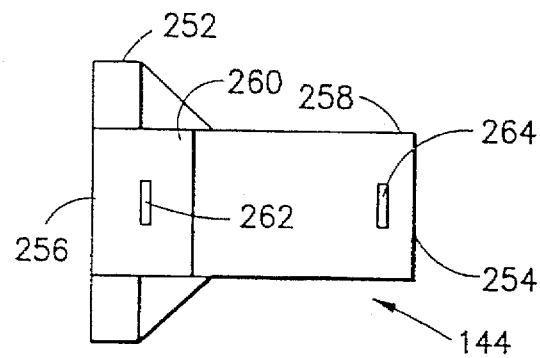
FIG. 12a is a top view of the coupling member as indicated by the line 12a—12a in FIG. 12.
Figure 12B:
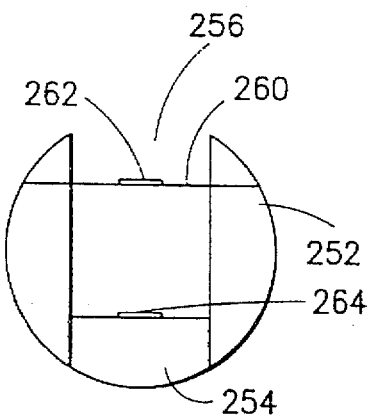
FIG. 12b is an end view of the coupling member as indicated by the line 12b—12b in FIG. 12.
Figure 12C:
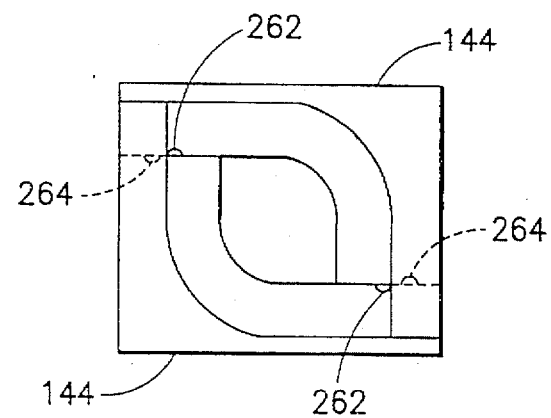
FIG. 12c is a view similar to FIG. 12 showing two engaged coupling members.
Figure 13:
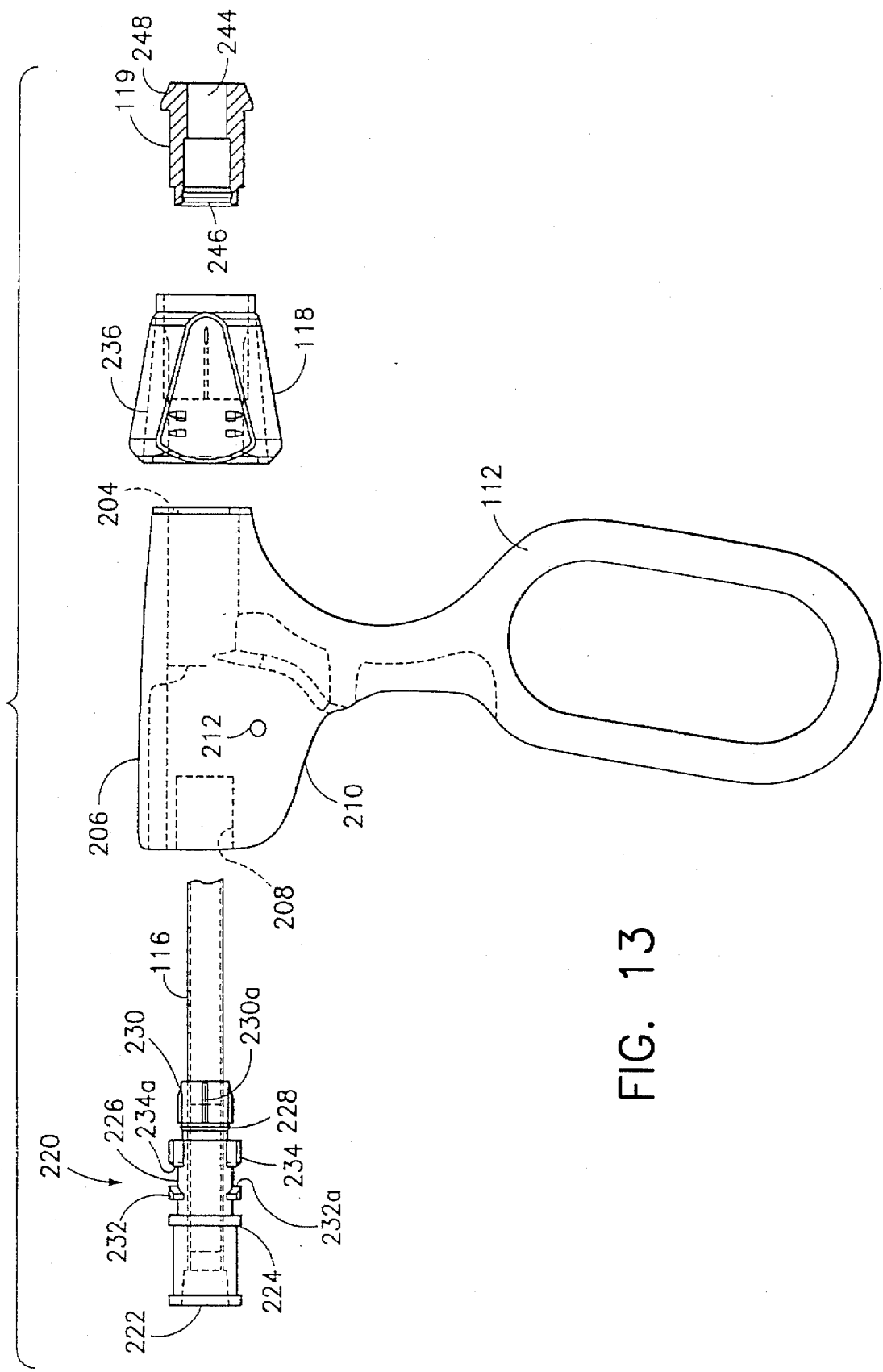
FIG. 13 is an exploded partially transparent and partially sectional side elevation view of some of the components of a second embodiment of the invention prior to assembly.
Figure 13A:
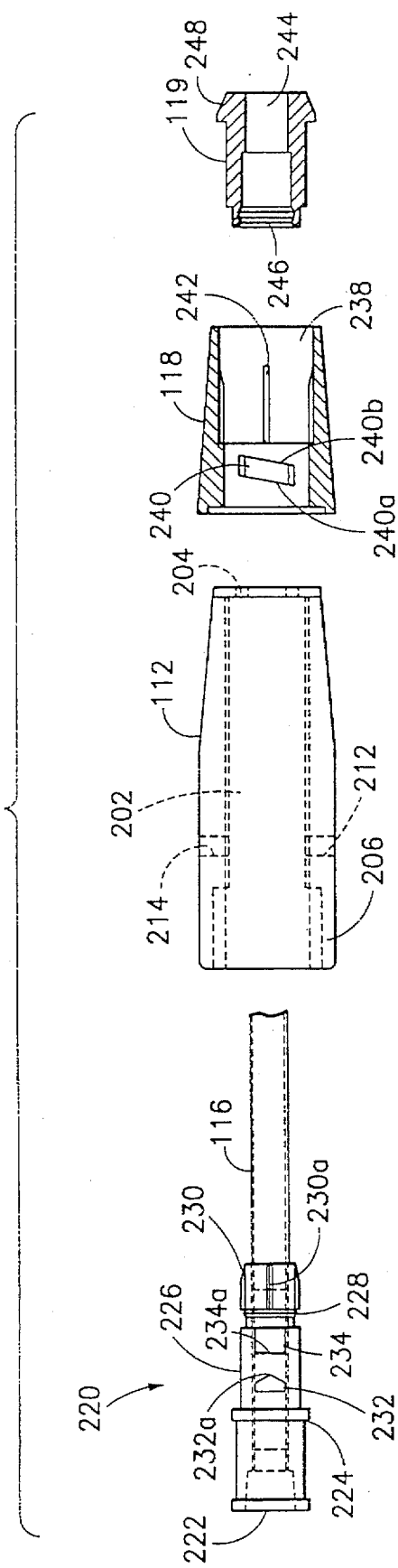
FIG. 13a is an exploded top view of the embodiment of FIG. 13.
Figure 13B:
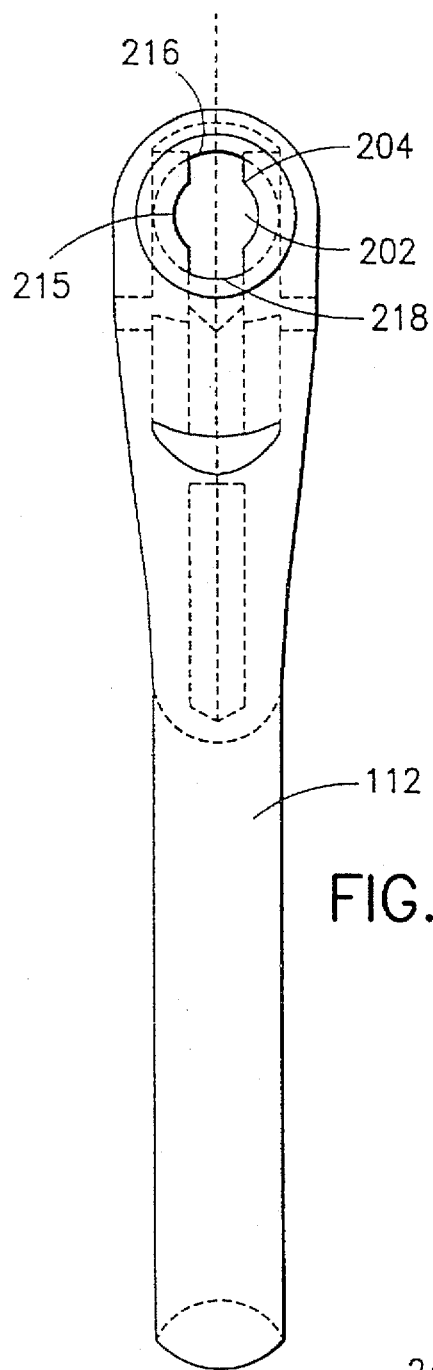
FIG. 13b is a distal end view of the handle of FIG. 13.
Figure 13C:
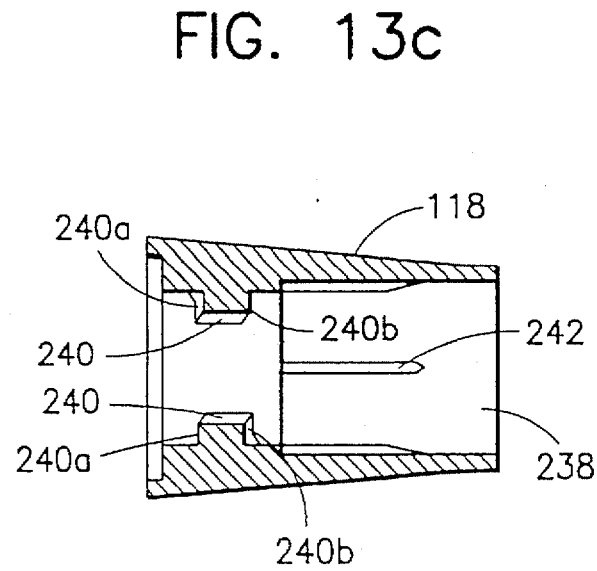
FIG. 13c is a longitudinal sectional view of the ferrule of FIG. 13.

Referring now to FIGS. 12 and 12a–12c, a push rod to lever coupling device is formed from two L-shaped members 144. Each member 144 has a circular base 252 with a tangentially extending leg 254. A portion of the base 252 has a circumferential notch 256 which is diametrically opposite to the leg 254. The dimensions of the notch 256 are substantially the same as the end portion 258 of the leg 254. The inner portion of the notch 256 is provided with a floor 260 which extends slightly beyond the base 252 in the same direction of the leg 254. A small ridge 262 is formed on the surface of the floor 260 and a similar ridge is formed on the inner surface 261 of the leg 254 near the end portion 258 of the leg. The inner surface 261 of the leg curves and extends substantially parallel to the base 252 ending at the floor 260 of the notch 256. As shown in FIG. 12c and as will be described in further detail below with reference to FIGS. 14 and 14a, two L-shaped members are symmetrically joined so that the end portion 258 of the leg 254 of one member 144 enters the notch 256 of another member 144.

Turning now to FIGS. 13, 13a, 13b, and 13c, the handle 112 of the second embodiment of the handle actuator 110 (FIGS. 15 and 15a) is provided with a through bore 202 with a distal keyway 204. The proximal end of the through bore 202 is formed as a hood 206 having a proximal opening 208 and a lower opening 210. Holes 212, 214 are provided in the lower portion of the hood for receiving a pivot pin as will be described below. As seen best in FIG. 13b, the distal keyway 204 is formed by a hole 215, which has a diameter smaller than the diameter of the through bore 202, and a pair of diametrically opposed slots 216, 218.

The proximal end of the tube 116 is press fit or preferably insert molded in a generally cylindrical sleeve 220. The sleeve 220 has an open proximal end 222 granting access to the interior of the tube 116, a centrally located annular stop 224, a reduced diameter keyed portion 226, an annular locking ring 228, and a distal splined portion 230. The diameter of the stop 224 is small enough to allow the sleeve 220 to pass through the through bore 202 of the handle 112, but large enough to prevent the sleeve 220 from passing through the distal keyway 204. The reduced diameter keyed portion 226 has a diameter small enough to pass through the hole 215 of the keyway 204 and is provided with two pair of radially extending and longitudinally spaced apart key members 232, 234 which are dimensioned to fit through the slots 216, 218 in the keyway 204. The proximal key members 232 are each preferably formed as a distally facing wedge having a central point 232a. The distal key members are formed with oppositely inclined proximal surfaces 234a providing the sleeve 220 with a thread-like nature.

A ferrule 118 is provided for engaging the keyed portion 226 of the sleeve 220 and a ferrule locking cylinder or cap 119 is provided for engaging the annular locking ring 228 and splined portion 230 of the sleeve 220 as described in more detail below. The ferrule 118 has a ribbed outer surface 236 and a central through bore 238. A proximal portion of the through bore 238 has a pair of radially inward extending projections 240 with proximal inclined surfaces 240a and distal inclined surfaces 240b. The inclination of the distal surfaces 240b corresponds to the inclination of surfaces 234a on the sleeve 220. The proximal inclined surfaces 240a may be provided with ridges (not shown) for engaging the central points 232a of the proximal key members 232 as described below. A distal portion of the through bore 238 has a plurality of radially inward extending splines 242. The ferrule locking cap 119 has a central through bore 244, a proximal inner locking groove 246, and a distal outer locking flange 248.

According to the second embodiment of the handle actuator of the invention, the instrument is assembled by first inserting the push rod through the hollow tube and attaching the end effectors as described above. After the end effectors are coupled to the tube and the push rod, the proximal end of the push rod is attached to the lever actuator as described below.

Figure 14:
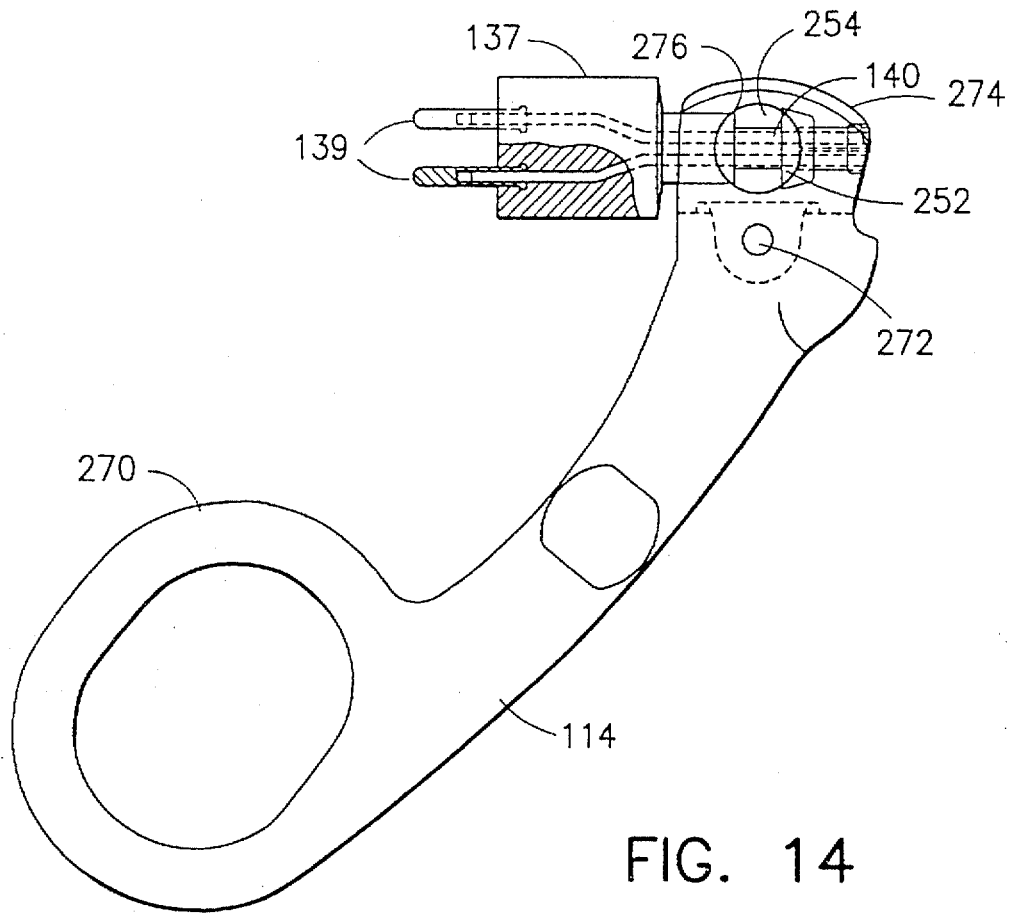
FIG. 14 is a broken side elevation view of a actuator lever for use with the second embodiment of the invention and showing the push rod assembly coupled to it.
Figure 14A:
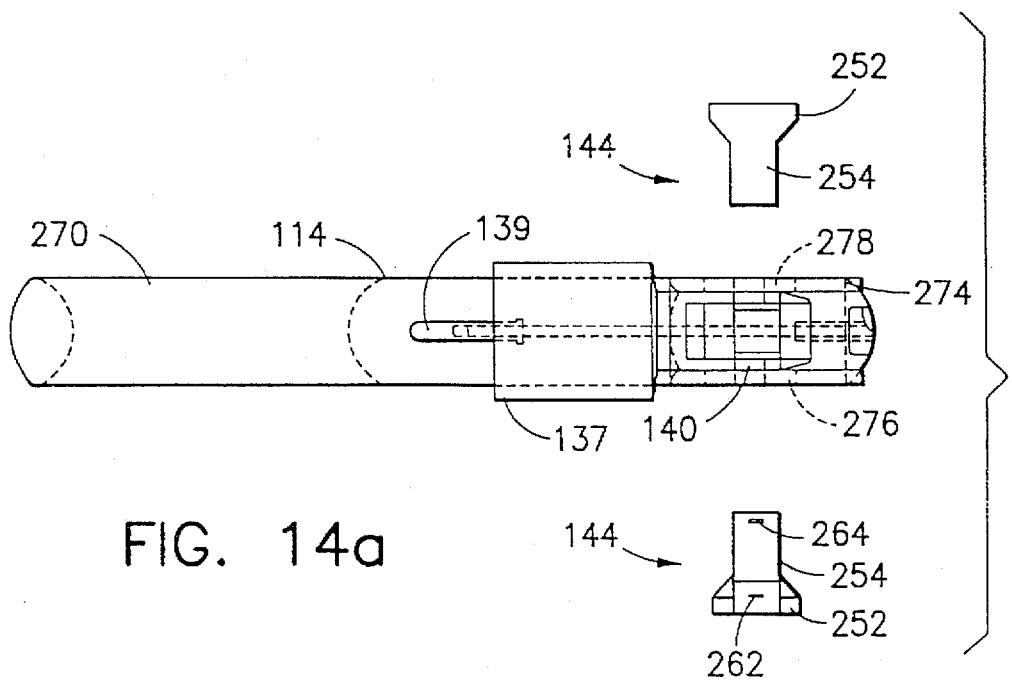
FIG. 14a is an exploded top view of the actuator lever of FIG. 14 with the push rod assembly and the coupling members of FIG. 12c.

As shown in FIGS. 14 and 14a, the lever actuator 114 of the second embodiment of the handle actuator 110 (FIGS. 15 and 15a) has a lower thumb ring 270, a pivot hole 272, and an upper U-shaped opening 274 which is transected by a bore defined by holes 276, 278. The push rod assembly is coupled to the lever actuator 144 by placing the proximal collar 136 in the U-shaped opening 274 so that the radial groove 140 is aligned with the holes 276, 278 substantially as shown. One of the L-shaped members 144 is inserted through hole 276 so that its leg 254 passes through the bottom of the groove 140 and the circular base 252 fits snugly flush with the hole 276. The other L-shaped member 144 is inserted through hole 278 so that its leg 254 passes through the top of groove 140 and its circular base 252 fits snugly flush with the hole 278. When the members 144 are in this position, which is substantially the same position relative to each other as shown in FIG. 14a, the ridge 264 on the leg of each member snaps over the ridge 262 on the floor of the notch of the other member. It will be appreciated that the engaged leg and notch for respective L-shaped members are held radially together by the inner circumference of the holes 276, 278. When held radially together, the ridges 262, 264 help prevent longitudinal separation of the members. It will further be appreciated that when the two members 144 are snapped together in this way, the proximal collar 136 of the push rod assembly is captured in the U-shaped opening of the lever 114, but the is still free to rotate about its longitudinal axis relative to the lever and is free to rotate somewhat relative to the pivot axis of the lever.

Figure 15:
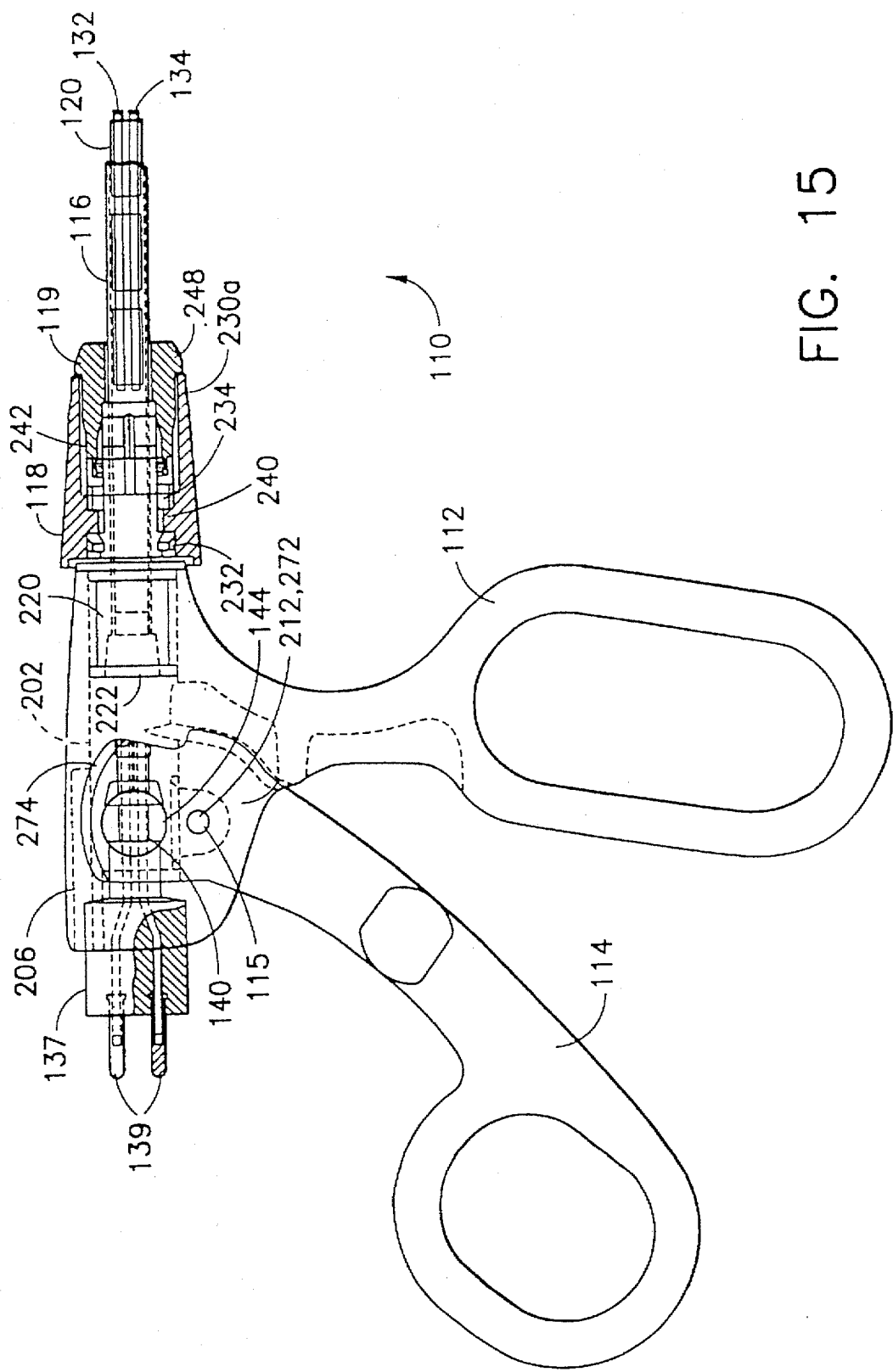
FIG. 15 is a transparent side elevation view in partial section showing the handle and actuator lever assembled.
Figure 15A:
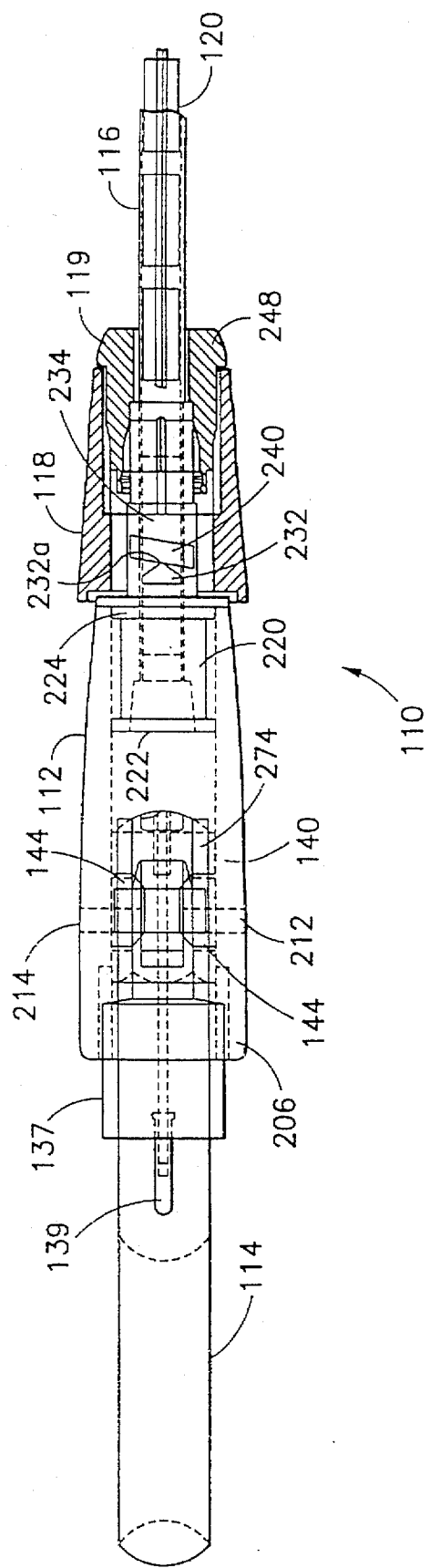
FIG. 15a is a top view of the assembled handle and actuator lever of FIG. 15.

Referring now to FIGS. 15 and 15a, assembly of the second embodiment of the handle actuator 110 is completed by inserting the end effectors (not shown), the tube 116, and the push rod 120 through the through bore 202 of the handle 112 until the sleeve 220 is stopped by the annular stop 224 and the key members 232, 234 extend through the keyway 204. The U-shaped opening 274 in the upper end of the lever actuator 114 is aligned with and inserted into the hood 206 in the handle 112. At this point, the pivot hole 272 in the lever actuator 114 may be aligned with the holes 212, 214 in the handle 112. A pivot pin 115 is inserted through holes 212, 272, and 214 thereby pivotally coupling the lever actuator 114 with the handle 112. It will be appreciated that when the lever actuator 114 is coupled to the handle 112 in this manner, the L-shaped members 144 are further prevented from disengagement with the push rod collar 136 because they are trapped between side walls of the hood 206 of the handle 112.

The ferrule 118 is then slid over the tube 116 and twisted onto the sleeve 220 so that the radially inward projections 240 on the ferrule 118 engage the key members 234 on the sleeve 220. The inclined surfaces of the projections 240 and the key members 234 cause the ferrule and the sleeve to be moved closer together as the ferrule is rotated in a screw-like manner. As seen best in FIG. 15a, this movement together between the sleeve 220 and the ferrule 118 is halted by the key members 232 when the distal wedge points 232a tightly engage the proximal surfaces 240a of the projections 240 of the ferrule 118. As mentioned above, surfaces 240a may be provided with ridges (not shown) to further enhance frictional engagement with the wedge points 323a. When the ferrule 118 and the sleeve 220 are thus engaged, rotation of the ferrule 118 results in rotation of the sleeve 220 and thus rotation of the tube 116 relative to the handle 112. Moreover, the space between the proximal end of the ferrule 118 and the stop 224 on the sleeve 220 is such that the ferrule and the sleeve engage the handle with some friction. After the ferrule and the sleeve are thus engaged, the polyethylene ferrule locking cap 119 is slipped over the tube 116 and forced into the distal end of the ferrule 118 until the locking groove 246 engages the locking ring 228 of the sleeve 220. In this position, the splines 230a on the splined end 230 of the sleeve 220 engage the inner surface of the through bore 244 of the locking cap 119 and the inner splines 242 in the distal portion of the ferrule through bore 238 engage the outer surface of the locking cap 119. The force fit of the relatively soft locking cap between the harder ferrule 118 and tube 220, and the distal flange 248 on the locking cap 119 both prevent the ferrule 118 from rotating out of engagement with the tube sleeve 220.

From the foregoing it will be appreciated that the second embodiment of the invention operates in substantially the same manner as the first embodiment. Movement of the lever actuator 114 relative to the handle 112 effects movement of the push rod assembly 120 through the tube 116, thus opening and closing the scissor blades (see FIG. 1). Rotation of the ferrule 118 relative to the handle 112 effects a rotation of the tube 116 and the scissor blades. Since the distal end of the push rod assembly is coupled to the scissor blades, rotation of the tube 116 also results in rotation of the push rod assembly 120. The L-shaped members 144 permit the push rod assembly 120 to be rotated relative to the handle 112 because the groove 140 in the proximal collar 136 is embraced by the legs of the L-shaped members. Moreover, any resistance which might be offered by the L-shaped members 144 will not risk any helical twisting of the rods 132, 134 because they are stabilized by the polypropylene cylinders 250, described above.

There have been described and illustrated herein several embodiments of a double acting bipolar endoscopic scissors having a handle with a ferrule arrangement for rotating the end effectors relative to the handle. While particular embodiments of the invention have been described, it is not intended that the invention be limited thereto, as it is intended that the invention be as broad in scope as the art will allow and that the specification be read likewise. Thus, while a particular handle and lever actuator has been disclosed, it will be appreciated that other types of endoscopic actuating means could be utilized with the bipolar scissors of the invention. Also, while particular insulators been shown at the clevis, it will be recognized that other types of insulators could be used with similar results obtained. Moreover, while particular configurations have been disclosed in reference to the collars, it will be appreciated that other configurations could be used as well. Furthermore, while the invention has been disclosed as having certain dimensions and specific materials, it will be understood that different dimensions and materials can achieve the same or similar function as disclosed herein. It will also be understood that the ferrule arrangement shown and described above with reference to FIGS. 11, 11a, 11b, 12, and 12a can be used with virtually any endoscopic instrument having a hollow tube and a push rod. It will be appreciated that when using other types of push rods, the proximal end of the push rod may be coupled to the lever actuator as shown herein or in any acceptable way known in the art. It will therefore be appreciated by those skilled in the art that yet other modifications could be made to the provided invention without deviating from its spirit and scope as so claimed.

We claim:

1. An actuator for an endoscopic instrument where the endoscopic instrument has a hollow tube with proximal and distal ends, a push rod with proximal and distal ends and extending through the hollow tube, and at least one end effector mounted for rotation at the distal end of the tube and coupled to the distal end of the push rod, said actuator comprising:

a) a handle having a through bore and a distal keyway, said keyway having a substantially circular central portion and at least one radially extending slot;

b) a tube sleeve which is adapted to be one of insert molded and press fit to the proximal end of the hollow tube, said tube sleeve having a proximal stop ring, a locking key, and a threading key;

c) a ferrule having a through bore and an interior threading member; and d) a lever pivotally coupled to said handle and adapted to be coupled to the proximal end of the push rod, wherein said tube sleeve extends through said keyway and is prevented from passing through said keyway by said proximal stop ring, said at least one radially extending slot allows passage of said locking key and threading key through said keyway, said interior threading member of said ferrule engages said threading key on said tube sleeve and is frictionally engaged by said locking key.

2. An actuator according to claim 1, wherein:
said locking key comprises a pair of radial extensions each having a distally facing frictional surface.

3. An actuator according to claim 2, wherein:
said threading key comprises a pair of radial extensions each having a proximally facing inclined surface.

4. An actuator according to claim 3, wherein:
said interior threading member comprises a pair of radially inward projections.

5. An actuator according to claim 1, further comprising:
e) a ferrule locking cap having a through bore, a proximal inner groove, and a distal flange, wherein
said tube sleeve has an annular ring distal of said threading key, said ferrule locking cap fits in an annular space between said tube sleeve and said ferrule, and said proximal inner groove engages said annular ring.

6. An actuator according to claim 5, wherein:
said tube sleeve has a plurality of exterior splines distal of said annular ring, said ferrule has a plurality of internal splines distal of said interior threading member, and said ferrule locking cap is frictionally engaged by said interior splines and said exterior splines.

7. An actuator according to claim 1, wherein:
said ferrule has a ribbed outer surface.

8. An actuator according to claim 1, wherein:
said lever has an upper U-shaped opening transected by a bore for engaging the proximal end of the push rod.

9. An actuator according to claim 8, further comprising:
e) a first L-shaped member having a first arm and a first circular base insertable in said bore in said lever for engaging a groove in the proximal end of the push rod with said first arm.

10. An actuator according to claim 9, further comprising:
f) a second L-shaped member having a second arm and a second circular base insertable in said bore in said lever for engaging a groove in the proximal end of the push rod with said second arm, said first and second L-shaped members each having an arm receiving notch in respective first and second circular bases.

11. An actuator according to claim 1, further comprising:
e) a ferrule locking cap having a through bore, wherein said ferrule locking cap is force fitted into an annular space between said tube sleeve and said ferrule.

12. An endoscopic instrument, comprising:
a) a hollow tube having a proximal and a distal end;
b) a push rod having a proximal and a distal end and extending through said hollow tube;
c) at least one end effector mounted for rotation at said distal end of said tube and coupled to said distal end of said push rod;
d) a handle having a through bore and a distal keyway, said keyway having a substantially circular central portion and at least one radially extending slot;
e) a tube sleeve which is one of insert molded and press fit to said proximal end of said hollow tube, said tube sleeve having a proximal stop ring, a locking key, and a threading key;
f) a ferrule having a through bore and an interior threading member; and
g) a lever pivotally coupled to said handle and coupled to said proximal end of said push rod, wherein
said tube sleeve extends through said keyway and is prevented from passing through said keyway by said proximal stop ring, said at least one radially extending slot allows passage of said locking key and threading key through said keyway, said interior threading member of said ferrule engages said threading key on said tube sleeve and is frictionally engaged by said locking key.

13. An endoscopic instrument according to claim 12, further comprising:
h) a ferrule locking cap having a through bore, wherein said ferrule locking cap force fits in an annular space between said tube sleeve and said ferrule.

14. An endoscopic instrument according to claim 13, wherein:
said ferrule locking cap has a proximal inner groove, and a distal flange, said tube sleeve has an annular ring distal of said threading key, and said proximal inner groove engages said annular ring.

15. A method for assembling an actuator for an endoscopic instrument where the endoscopic instrument has a hollow tube with proximal and distal ends, a push rod with proximal and distal ends and extending through the hollow tube, and at least one end effector mounted for rotation at the distal end of the tube and coupled to the distal end of the push rod, said method comprising:
a) obtaining a handle having a through bore and a distal keyway, said keyway having a substantially circular central portion and at least one radially extending slot;
b) obtaining a tube sleeve having a proximal stop surface, a locking key, and a threading key;
c) coupling said tube sleeve to the proximal end of the hollow tube by one of insert molding and press fitting;
d) obtaining a lever with means for coupling to the push rod and means for coupling to said handle;
e) coupling said lever to the proximal end of the push rod;
f) inserting the hollow tube through said through bore in said handle so that said tube sleeve extends through said keyway but is prevented from passing through said keyway by said proximal stop surface, said at least one radially extending slot allowing passage of said locking key and threading key through said keyway;
g) pivotally coupling said lever to said handle;
h) obtaining a ferrule having a through bore and an interior threading member; and
i) sliding said ferrule over the distal end of said tube and threading said interior threading member of said ferrule on to said threading key of said tube sleeve until said threading member is frictionally engaged by said locking key.

16. A method according to claim 15, further comprising:
j) obtaining a ferrule locking cap; and
k) sliding said ferrule locking cap over the distal end of the tube and force fitting said ferrule locking cap into an annular space between said ferrule and at least one of said tube sleeve and the hollow tube.

17. An endoscopic instrument, comprising:
a) a hollow tube having a proximal and a distal end;

b) a push rod having a proximal and a distal end and extending through said hollow tube;

c) at least one end effector mounted for rotation at said distal end of said tube and coupled to said distal end of said push rod;

d) a handle having a through bore with a reduced diameter distal end;

e) a tube sleeve which is fixed to said proximal end of said hollow tube, said tube sleeve having a proximal stop surface and a distal exterior frictional engagement member;

f) a ferrule having a through bore and an interior frictional engagement member; and g) a lever pivotally coupled to said handle and coupled to said proximal end of said push rod, wherein said tube sleeve extends through said through bore and is prevented from passing entirely through said through bore by said proximal stop ring surface, said interior frictional engagement member of said ferrule frictionally engages said distal exterior frictional engagement member, one of said interior frictional engagement member of said ferrule and said exterior frictional engagement member of said tube sleeve having a locking structure which engages the other of said interior frictional engagement member of said ferrule and said exterior frictional engagement member of said tube sleeve and prevents rotational movement of said ferrule relative to said tube sleeve, such that rotation of said ferrule causes rotation of said tube sleeve and said hollow tube relative to said handle.

18. An endoscopic instrument according to claim 17, wherein:

one of said distal exterior frictional engagement member and said interior frictional engagement member includes at least two longitudinally spaced apart non-contiguous radial surface projections, and the other of said distal exterior frictional engagement member and said interior frictional engagement member includes a threading member.

19. An endoscopic instrument according to claim 18, wherein:

said at least two longitudinally spaced apart radial surface projections includes a locking key and a threading key.

20. An endoscopic instrument according to claim 19, wherein:

said at least two longitudinally spaced apart radial surface projections includes a pair of diametrically opposed locking keys and a pair of diametrically opposed threading keys, and said interior threading member includes two diametrically opposed interior threading members.

\* \* \* \* \*